United States Patent
McClellan et al.

(10) Patent No.: US 10,076,458 B2
(45) Date of Patent: Sep. 18, 2018

(54) HOSPITAL BED HAVING MODULAR POWER/DATA HUB

(71) Applicants: Aaron McClellan, Lebanon, NH (US); Ryan C. Stockett, Lebanon, NH (US)

(72) Inventors: Aaron McClellan, Lebanon, NH (US); Ryan C. Stockett, Lebanon, NH (US)

(*) Notice: Subject to any disclaimer, the term of this patent is extended or adjusted under 35 U.S.C. 154(b) by 1 day.

(21) Appl. No.: 15/594,873

(22) Filed: May 15, 2017

(65) Prior Publication Data
US 2017/0337797 A1 Nov. 23, 2017

Related U.S. Application Data

(60) Provisional application No. 62/338,989, filed on May 19, 2016.

(51) Int. Cl.
*A61G 7/05* (2006.01)
*A61G 12/00* (2006.01)
*H04Q 1/00* (2006.01)

(52) U.S. Cl.
CPC ............. *A61G 7/05* (2013.01); *A61G 12/008* (2013.01); *H04Q 1/00* (2013.01)

(58) Field of Classification Search
CPC .... G08B 21/0446; G08B 25/08; A61G 12/00; A61G 7/00; A61G 2203/12; A61G 2203/70; H04Q 1/00
USPC .................................................. 340/573.1
See application file for complete search history.

(56) References Cited

U.S. PATENT DOCUMENTS

| | | | |
|---|---|---|---|
| 4,895,161 A | 1/1990 | Cuhahy et al. | |
| 5,687,717 A | 11/1997 | Halpern et al. | |
| 6,221,012 B1 | 4/2001 | Maschke et al. | |
| 2003/0009825 A1* | 1/2003 | Gallant | A61G 1/00 5/81.1 R |
| 2003/0056971 A1 | 3/2003 | Wechsler | |
| 2004/0147818 A1 | 7/2004 | Levy et al. | |
| 2017/0221344 A1* | 8/2017 | Cox | G08B 25/008 |
| 2017/0259051 A1* | 9/2017 | Palmer | A61J 7/0053 |

* cited by examiner

*Primary Examiner* — Tanmay Shah
(74) *Attorney, Agent, or Firm* — Ryan C. Stockett

(57) ABSTRACT

A data hub is disclosed for use with a hospital bed. The data hub may have a base mountable on the hospital bed, and a collection module dockable with the base. The base may include a stationary base housing, a power supply link extending into the stationary base housing, and a data link extending into the stationary base housing and being connectable to an external monitoring station. The collection module may include a module housing, a plurality of inlet data ports formed in the module, at least one outlet port formed in the module housing, a medium supply disposed in the module housing and connected to the at least one outlet port, and an adapter disposed in the module housing and configured to connect the plurality of inlet data ports to the data link and the power supply link upon docking of the module housing with the stationary base housing.

19 Claims, 3 Drawing Sheets

HOSPITAL BED HAVING MODULAR POWER/DATA HUB

RELATED APPLICATIONS

This application is based on and claims priority to U.S. Provisional Application No. 62/338,989 filed on May 19, 2016, the contents of all of which are expressly incorporated herein by reference.

TECHNICAL FIELD

The present disclosures relates generally to a hospital bed and a monitoring system and, more particularly, to a hospital bed having a modular power/data hub.

BACKGROUND

When a patient is admitted to a medical care facility, the patient is often connected to multiple different devices used to monitor the health of the patient. For example, the patient can be connected to a Hood pressure monitor, a respiration monitor, a heart monitor, a temperature monitor, a blood-oxidation monitor, and other types of monitors. These various monitoring devices are often co-located within a bedside chassis. The bedside chassis can be large and bulky, and requires one or more leads (e.g., power leads, sensor leads, pneumatic leads, etc.) that extend from each monitoring device to the patient.

While the conventional health monitoring device may be acceptable for some applications, it can also be problematic. In particular, it is often necessary to move the patient between different locations at the medical care facility. For example, the patient may move from a triage area to an ER area, from the ER area to a radiology area, from the radiology area to a surgical area, from the surgical area to a recovery area, from the recovery area to a patient room, etc. Because of the size and/or bulkiness of the monitoring devices, the patient is generally disconnected from the devices in a first area prior to transport and reconnected to the devices in a next area after transport. This disconnecting and reconnecting can be time- and labor-intensive and also provide opportunity for error in the reconnecting. Further, the health of the patient may not be adequately monitored during the transport between areas.

An alternative solution is disclosed in U.S. Pat. No. 4,859,161 of Cudahy et al. that issued on Jan. 23, 1990 ("the '161 patent"). In particular, the '161 patent discloses a monitoring system including a data acquisition and processing module that receives physiological data from a patient via a plurality of wires. The module may be inserted into a bedside display unit to display the physiological data being monitored. The module may also be inserted into a portable display unit that can accompany the patient during transport. Connectors permit the module to simultaneously drive both of the display units so that no data is lost when the module is removed from the bedside unit and placed in the portable unit.

While the monitoring system of the '161 patent may reduce a need to disconnect and reconnect the various leads from and to the patient during transport between areas at the medical care facility, the system may still be less than optimal. In particular, the system still requires the same number of leads to extend from the patient to the display units, which can take a significant amount of space around the patient (and also around the bed, table, gurney, etc. at each location). In addition, the large number of leads connecting to the display unit can create opportunities for misconnection, entanglement, inadvertent snagging and disconnection, etc. Further, the module of the '161 patent may not be equipped to handle all of the monitoring needs of the patient. For example, in order to continuously monitor blood pressure, pressurized air must be supplied to a cuff on the patient. The module of the '161 patent is not capable of providing for this need.

The hospital bed and hub of the present disclosure solves one or more of the problems set forth above and/or other problems in the art.

SUMMARY

In one aspect, the present disclosure is directed to a data hub for a hospital bed. The data hub may include a base mountable on the hospital bed. The base may include a stationary base housing, a power supply link extending into the stationary base housing, and a data link extending into the stationary base housing and being connectable to an external monitoring station. The data hub may also include a collection module configured to dock with the base. The collection module may include a module housing configured to engage the stationary base housing during docking, a plurality of inlet data ports formed in the module, at least one outlet port formed in the module housing, a medium supply disposed in the module housing and connected to the at least one outlet port, and an adapter disposed in the module housing and configured to connect the plurality of inlet data ports to the data link and to the power supply link upon docking of the module housing with the stationary base housing.

In another aspect, the present disclosure is directed to another data hub for a hospital bed. This data hub may include a base mountable on the hospital bed. The base may include a stationary base housing, a power supply link extending into the stationary base housing, and a single data cable extending into the stationary base housing and being connectable to a plurality of monitoring devices at an external monitoring station. The data hub may also include a collection module configured to dock with the base. The collection module may include a module housing configured to engage the stationary base housing during docking, a plurality of inlet data ports formed in the module housing, and an adapter disposed in the module housing and configured to connect the plurality of inlet data ports to at least one of the single data cable and the power supply link upon docking of the module housing with the stationary base housing.

In yet another aspect, the present disclosure is directed to a hospital bed. The hospital bed may include a support structure, a frame moveable relative to the support structure, a power supply link, and an actuator powered by the power supply link to move the frame. The hospital bed may also include a data hub having a base powered by the power supply link and operatively mounted to at least one of the support structure and the frame. The base may include a data link connectable to an external monitoring station. The hospital bed may further include a collection module configured to dock with the base and including a plurality of inlet data ports, and an adapter configured to connect the plurality of inlet data ports to the data link upon docking of the collection module with the base.

In a final aspect, the present disclosure is directed to method of monitoring health of a patient. The method may include connecting first ends of a plurality of data leads to the patient, connecting a blood pressure cuff to the patient, connecting second ends of the plurality of data leads and an air supply hose of the blood pressure cuff to a collection module, and connecting a single cable from a bed of the patient to a monitoring station. The method may also include docking the collection module to the bed to power the collection module, to communicate the plurality of data leads with the monitoring station via the single data cable, and to supply the blood pressure cuff with pressurized air.

DETAILED DESCRIPTION

Figure 1:
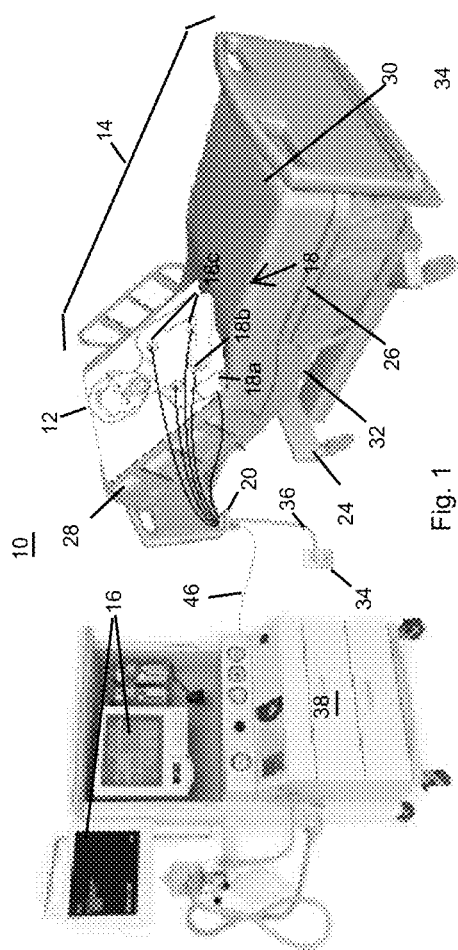
FIG. 1 is a perspective illustration of an exemplary disclosed monitoring system and hospital bed.

FIG. 1 illustrates an exemplary system 10 that may be used to monitor the health of a patient 12, while the patient is supported by a hospital bed 14. System 10 may include, among other things, a plurality of monitoring devices 16 configured to receive, record, interpret, analyze, process, and/or display signals captured by any number of different sensors 18 connected to the patient 12. Sensors 18 may be connected to monitoring devices 16 by way of a data hub 20.

For the purposes of this disclosure, hospital bed 14 may be broadly interpreted as any type of structure configured to support the patient, while the patient is inside a medical care facility. In one embodiment, hospital bed 14 is a conventional bed located in a patient's room. However, in other embodiments, a surgical table, a gurney, a radiological platform, or another similar type of structure may be construed as hospital bed 14.

In the example of FIG. 1, hospital bed 14 includes a lower support structure 24, and an upper frame 26 that is operatively connected to lower support structure 24. Lower support structure 24 may be a stationary type of structure having one or more legs, or a mobile type of structure having one or more wheels. Many different configurations may be available.

Upper frame 26 may be movable relative to lower support structure 24. For example, a head portion 28 of frame 26 may be tilted up or down; a foot portion 30 may be tilted up or down; and/or all of upper frame 26 may be raised or lowered, as desired. Any number of actuators 32 may be connected between lower support structure 24 and upper frame 26 and operable to cause the relative movements described above. Actuators 32 may embody motors, pistons, screws, or other types of actuators that are electrically powered by an established utility grid 34 via a power supply link 36.

Monitoring devices 16 may be mobile or stationary and located on bed 14, adjacent bed 14, and/or remote from bed 14. In the disclosed example, monitoring devices 16 are co-located within a common chassis 38, although separate stand-alone devices may also be used. Exemplary monitoring devices includes display screens (e.g., CRT, LED, and/or LCD screens), digital readouts (numerical readouts of maximum values, minimum values, average values, rates, frequencies, etc.), oscilloscopes (e.g., time-indexed analog tracers), and other types of monitoring devices known in the art. In one embodiment, monitoring devices 16 are dedicated to relaying a single type of information. In other embodiments, however, a single monitoring device 16 may have multiple display sections; each section configurable to relay one or more types of information. Exemplary information that could be relayed by monitoring devices 16 include respiration rate, pulse oximetry, pulse rate, blood pressure, blood flow, body temperature, cardiac rhythm, capnography, intracranial pressure, blood glucose, etc. This information may be generated directly by sensors 18 or determined based on a combination of signals received from any number of different sensors 18.

Sensors 18 may be directly connected to the patient 12 or indirectly connected to the patient 12 via any number of electrical leads. In the disclosed embodiment, exemplary sensors include a blood pressure arm cuff 18a, a pulse-oximetry finger cuff 18b, and a plurality of cardiography electrodes 18c. It is contemplated that any number and types of sensors 18 may be used in conjunction with system 10. As will be explained in more detail below, signals generated by sensors 18 may be directed to monitors 16 via hub 20. In some embodiments, sensors 18 may also be powered via hub 20.

Figure 2:
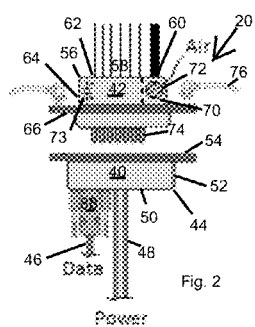
FIG. 2 is a diagrammatic illustration of an exemplary disclosed hub that may be used in conjunction with the monitoring system and hospital bed of FIG. 1.

An exemplary hub 20 is illustrated in FIG. 2. As shown in this figure, hub 20 may include, among other things, a base 40 and a collection module 42. Base 40 may generally be stationary and mounted to integral with) hospital bed 14, while collection module 42 may be selectively docked with any number of similarly configured bases 40 in association with the particular hospital bed 14 currently supporting the patient 12. In other words, once sensors 18 are connected to the patient, collection module 42 may travel with the patient and connect to which ever base 40 is available in the area where the patient 12 is currently located.

Base 40 may generally include a base housing 44, a data link 46, and a power link 48. Base housing 44 may embody an enclosed structure mounted to hospital bed 12 (e.g., to a headboard, support structure 24, or frame 26) and consist of an end wall 50, a plurality of side walls 52 protruding away from end wall 50, and a connection face 54 located opposite end wall 50. Data and power links 46, 48 may connect with base housing 44, for example at end wall 50. In this configuration, data link 46 may extend between end wall 50 and chassis 38, while power link 48 may either extend between end wall 50 and an actuator 32 of hospital bed 10 or between end wall 50 and utility grid 34. In the latter embodiment, power link 36 of a particular actuator (26) may connect with power link 48 inside base housing 44 to receive power via base 40. Other configurations may also be possible, as long as hub 20 and actuators 32 receive power from the same source (e.g., from a single outlet via a single plug).

Collection module 42 may include a module housing 56, a plurality of input data ports 58, and at least one outlet port 60. Module housing 56 may embody an enclosed structure removably connectable to base 40 and consist of an end wall 62, a plurality of side walls 64 protruding away from end wall 62, and a connection face 66 located opposite end wall 62. A plurality of electrical leads associated with sensors 18 may connect with input data ports 58, for example at end wall 62. In this configuration, the leads may extend between sensors 18 and module housing 56. Outlet port 60 may be configured to pass a medium to a particular sensor 18 to facilitate operation of the sensor 18. In the disclosed embodiment, outlet port 60 is associated with blood pressure cuff 18a and configured to pass a pressurized gas, for example, to blood pressure cuff 18a via a corresponding hose. It is contemplated, however, that another medium may be passed through outlet port 60 for the same or another purpose, if desired.

The medium passed through outlet port 60 may be supplied from one of two different sources. In the embodiment of FIG. 2, the source of the medium is itself disposed inside of module housing 56. In particular, an air pump 70 may be mounted inside module housing 56 and configured to draw ambient air in through a vent 72 provided in side wall 64, to pressure the air, and to direct the pressurized air to the corresponding sensor 18a via outlet port 60 and associated hose. In this configuration, air pump 70 may be powered via power link 48 and controlled via data link 46. It is contemplated that air pump 70 could alternatively be both controlled and powered via data link 46. In a second embodiment, the supply of pressurized air could alternatively be located on chassis 38 (referring to FIG. 1). In particular, pressurized air could be supplied to hub 20 via data link 46, and only relayed to blood pressure cuff 18a via outlet port 60 and the associated hose.

In some embodiments, during re-docking of control module 42 from a first base 40 to a second base 40, sensors 18, pump 70, and/or another part of control module 42 may still require electrical power. In these embodiments, control module 42 may be provided with a power storage device (e.g., a battery) 73. Battery 73 may be selectively or continuously charged via power link 48 when control module 42 is docked to base 40.

Base 40 may function as a docking station for control module 42, by proving mechanical support, electrical power, and data communication. In the disclosed embodiment, an adapter 74 may facilitate this connection. Adapter 74 may take any form known in the art. For example, adapter 74 may include a first (e.g., female) part formed within or otherwise attached to connection face 54 of base housing 44 that is configured to receive a second (e.g., male) part formed within or otherwise attached to connection face 66 of module housing 56. When the first and second parts of adapter 74 are coupled, electrical connections may be established between sensors 18 and data and power links 46, 48. In addition, the coupling of the first and second parts of adapter 74 may facilitate the passing of pressurized air to blood pressure cuff 18a, in some embodiments.

The docking of control module 42 to base 40 may be established in any number of different ways. In the disclosed embodiment, connection faces 54 and 66 are shown as simply abutting each other, and then being held in this position via one or more locking mechanisms 76. In other embodiments, however, control module 42 could additionally or alternatively be received within a corresponding recess (not shown) of base 40, or vice versa. Other ways to dock control module 42 with base 40 may also be used.

Figure 3:
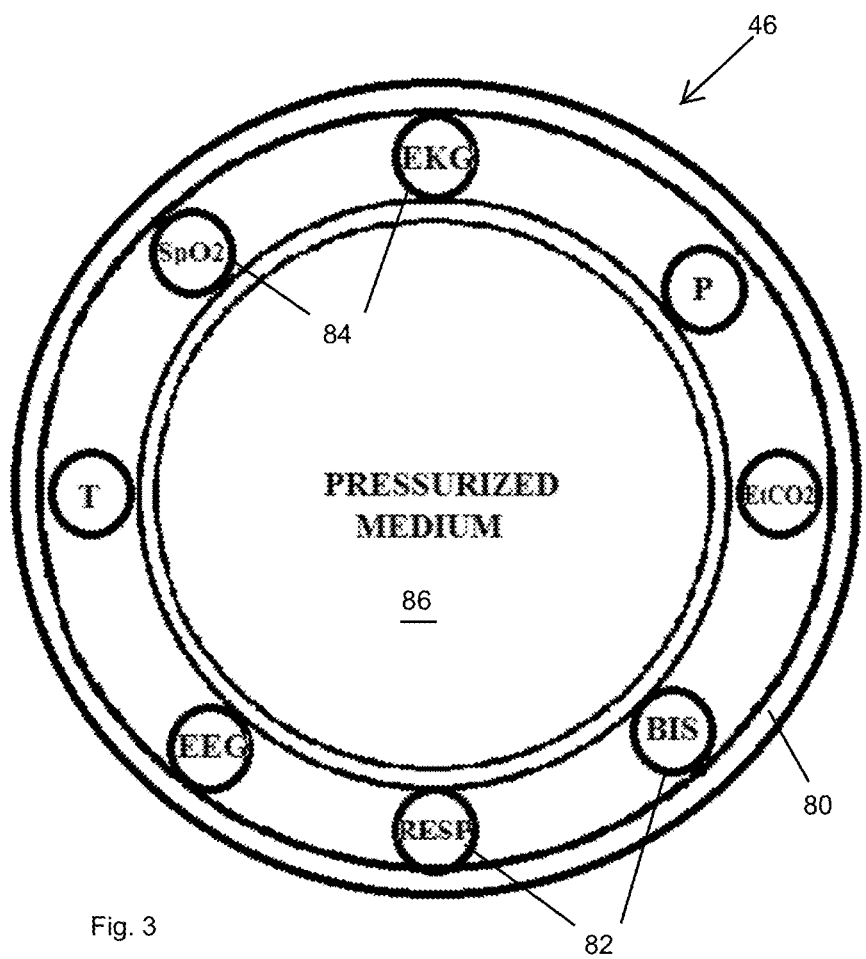
FIG. 3 is a cross-sectional illustration of an exemplary disclosed cable that may be used in conjunction with the hub of FIG. 2.

FIG. 3 illustrates a cross-sectional view of an exemplary embodiment of data link 46. As can be seen in this example, data link 46 may be multi-functional, yet consist of a single cable. For example, a single outer sheath 80 may encapsulate any number of different signal wires 82, power leads 84, and/or medium conduits 86, as desired. An appropriate connector 88 (shown in FIG. 2) may be located at each end of data link 46, allowing the single cable to mechanically connect with hub 20 and monitoring devices 16 (e.g., via chassis 38), while at the same time separately connecting each of wires 82, leads 84, and conduits 86 with their corresponding sources and destinations.

INDUSTRIAL APPLICABILITY

The disclosed hospital bed and data hub may reduce the time and effort involved in moving a patient between areas within a medical care facility. In addition, the disclosed hospital bed may reduce errors associated with instrumenting a patient, while also improving the use of space around the patient. The use of hospital bed 10 and hub 20 will now be described, with reference to FIGS. 1 and 2.

When a patient is received at the medical care facility and requires health monitoring, the patient may be instrumented with any number of different sensors. This process may include, among other things, the connecting of sensors 18 to the patient 12. For example, blood pressure cuff 18a may be wrapped around the patient arm, the finger cuff 18b may be placed over the patients index finger, and the electrodes 18c may be placed at the appropriate positions on the patient's chest and abdomen. Thereafter, corresponding leads 58 may be connected between these sensors 18 and input ports 58 within collection module 42. In addition, in some instances, a hose may be connected between outlet port 56 and blood pressure cuff 18b. The single cable of data link 46 may then be connected between base 40 and monitors 16 and/or chassis 38 (together considered a monitoring station). Collection module 42 may then be docked with base 40 mounted on the particular hospital bed 10 currently supporting the patient 12, thereby powering collection module 42 and establishing communication between sensors 18 and monitors 16 and between pump 70 and blood pressure cuff 18a. Thereafter, any time the patient must be moved to a different hospital bed 10, collection module 42 may simply be undocked from base 40 of the first hospital bed 10, and then re-docked with a different base 40 of the next hospital bed 10.

The disclosed hub 20 may reduce the time and effort involved with moving the patient 12 between hospital beds. In particular, hub 20 may allow all sensors and corresponding leads to remain in place. In addition to the reduction in time and effort achieved by leaving sensors 18 in place during the patient move, the reduced number of connection/disconnections involved may also help to reduce the likelihood of making these connections/disconnects incorrectly. Further, the single cable extending between hub 20 and chassis 38 may free up space surrounding the patient 12.

It will be apparent to those skilled in the art that various modifications and variations can be made to the disclosed bed and hub without departing from the scope of the disclosure. Other embodiments of the bed and hub will be apparent to those skilled in the art from consideration of the specification and practice of the system disclosed herein. It is intended that the specification and examples be considered as exemplary only, with a true scope of the disclosure being indicated by the following claims and their equivalents.

What is claimed is:

1. A data hub for a hospital bed, comprising:
   a base housing removably mountable on the hospital bed;
   a power supply link extending into the base housing;
   a data link extending into the base housing and being connectable to an external monitoring station;
   a module housing configured to engage the base housing during docking;
   a plurality of patient inlet data ports formed in the module housing;
   at least one outlet port formed in the module housing;
   a medium supply disposed in the module housing and connected to the at least one outlet port; and
   an adapter disposed in the module housing and configured to connect the plurality of patient inlet data ports to the data link and to the power supply link upon docking of the module housing with the base housing.

2. The data hub of claim 1, wherein the data link includes a single cable configured to communicate all of the plurality of patient inlet data ports with the external monitoring station.

3. The data hub of claim 1, wherein the medium supply is configured to supply pressurized air to the at least one outlet port.

4. The data hub of claim 3, wherein the medium supply is a pump disposed in the module housing and powered by the power supply link in the base housing via the adapter.

5. The data hub of claim 4, further including a battery chargeable by the power supply link via the adapter and configured to power the pump when the module housing is undocked from the base housing.

6. The data hub of claim 1, further including a locking device configured to secure the module housing to the base housing.

7. A data hub for a hospital bed, comprising:
a base housing removably mountable on the hospital bed;
a power supply link extending into the base housing;
a single data cable extending into the base housing and being connectable to a plurality of monitoring devices at an external monitoring station;
a module housing configured to engage the base housing during docking;
a plurality of patient inlet data ports formed in the module housing; and
an adapter disposed in the module housing and configured to connect the plurality of patient inlet data ports to at least one of the single data cable and the power supply link upon docking of the module housing with the base housing.

8. The data hub of claim 7, including:
an air pump disposed in the module housing and powered by the power supply link in the base housing via the adapter; and
an outlet port formed in the module housing and fluidly communicated with the air pump.

9. The data hub of claim 8, further including a battery chargeable by the power supply link via the adapter and configured to power the pump when the module housing is undocked from the base housing.

10. The data hub of claim 7, further including a locking device configured to secure the module housing to the base housing.

11. The data hub of claim 7, wherein the single cable includes a plurality of separate data links associated with the plurality of input data ports.

12. The data hub of claim 11, wherein:
the single cable further includes an air conduit configured to communicate a supply of pressurized air from the external monitoring station with the base housing;
the collection module further includes an outlet port formed in the module housing; and
the adapter is configured to pass the supply of pressurized air from the base housing to the outlet port.

13. A hospital bed, comprising:
a support structure;
a frame moveable relative to the support structure;
a power supply link;
an actuator powered by the power supply link to move the frame; and
a data hub powered by the power supply link and including:
a base housing removably mounted to at least one of the support structure and the frame;
a data link disposed in the base housing and connectable to an external monitoring station;
a module housing configured to dock with the base housing and including a plurality of patient inlet data ports; and
an adapter configured to connect the plurality of patient inlet data ports to the data link upon docking of the module housing with the base housing.

14. The hospital bed of claim 13, wherein the data link includes a single cable configured to communicate all of the plurality of patient inlet data ports with the external monitoring station.

15. The hospital bed of claim 14, wherein the single cable includes a plurality of separate data links associated with the plurality of patient input data ports.

16. The hospital bed of claim 15, wherein:
the single cable further includes an air conduit configured to communicate a supply of pressurized air from the external monitoring station with the base housing;
the data hub further includes an outlet port formed in the module housing; and
the adapter is configured to pass the supply of pressurized air from the base housing to the outlet port.

17. The hospital bed of claim 13, wherein the data hub further includes:
an air pump powered by the power supply link in the base housing via the adapter; and
an outlet port in fluid communication with the air pump.

18. The hospital bed of claim 15, wherein the data hub further includes a battery chargeable by the power supply link via the adapter and configured to power the pump when the module housing is undocked from the base housing.

19. The hospital bed of claim 13, further including a locking device configured to secure the module housing to the base housing.

* * * * *